Nov. 10, 1970 R. KORDES Plant Pat. 2,999
ROSE PLANT
Filed Feb. 19, 1969
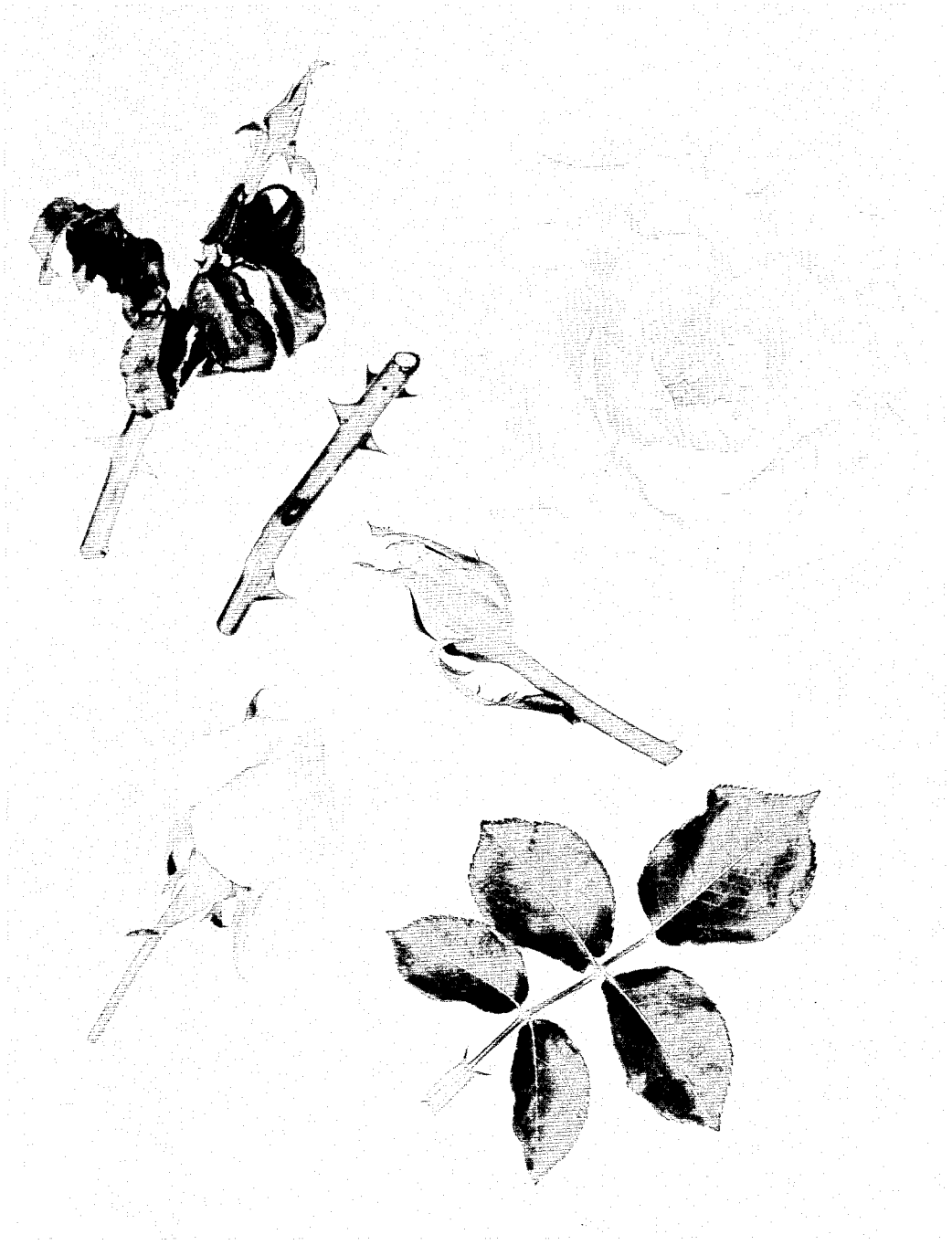
Inventor.
Reimer Kordes
By: Robb & Robb
Attorneys.

United States Patent Office

Plant Pat. 2,999
Patented Nov. 10, 1970

2,999
ROSE PLANT

Reimer Kordes, Barmstedt, near Elmshorn, Germany, assignor to Jackson & Perkins Company, Newark, N.Y., a corporation of New York

Filed Feb. 19, 1969, Ser. No. 800,780
Int. Cl. A01h *5/00*
U.S. Cl. Plt.—16 1 Claim

The present invention relates to a new and distinct variety of rose plant of the hybrid tea class, which was originated by me by crossing the rose variety known as "Chantre" (unpatented) with the rose variety known as "Charming Vienna" (U.S. Plant Pat. No. 2,550).

The primary objective of this breeding was to produce a new rose variety which bears uniformly colored flowers of orange color and of good form and substance. This objective was fully achieved, along with other desirable improvements, as evidence by the following unique combination of characteristics which are outstanding in the new variety and which distinguish it from its parents, as well as from all other rose varieties of which I am aware:

(1) An upright plant habit;

(2) A habit of bearing the flowers on long and strong stems;

(3) Distincitvely well-formed flowers of good substance, said flowers being high-centered in the early stages, while being of imbricated form when fully open; and (4) A distinctive, attractive and uniform orange flower color.

Asexual reproduction of my new variety by budding, as performed by me in Germany and on my behalf at Livermore, Calif., U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new rose variety, with color terminology in accordance with Ridgway's Color Standards and Nomenclature, except where general color terms of ordinary dictionary significance are obvious:

Parentage: Seedling.
*Seed parent.*—"Chantre."
*Pollen parent.*—"Charming Vienna."
Classification:
*Botanic.*—Rosa hybrid.
*Commercial.*—Hybrid tea.
Propagation: Holds its distinguishing characteristics through succeeding propagations by budding.

FLOWER (Observations made from specimens grown at Newark, N.Y., U.S.A., in the afternoon during late September).

Blooming habit:
*Recurrent.*—Continuous.
Bud:
*Size.*—Medium.
*Form.*—Pointed; ovoid.
*Color.*—When sepals first divide: Ochraceous Orange, Plate XV, 15′. When half-blown: Ocharecous Orange, Plate XV, 15′. Reverse of petals: Ochraceous Orange, Plate XV, 15′.
*Sepals.*—Nearly smooth edge; 2 sepals have nearly smooth edge, and other 3 sepals have small foliaceous appendages. Color: Inside—Biscay Green, Plate XVII, 27′, covered with gray tomentum. Outside—Biscay Green, Plate XVII, 27′.
*Receptable.*—Color: Biscay Green, Plate XVII, 27′–i. Shape: Funnel. Size: Large. Surface: Smooth.
*Peduncle.*—Length: Medium. Strength: Stiff.
*Opening.*—Edges of sepals roll open.

Bloom:
*Size.*—Large. Average size when fully expanded: From 3½ inches to 4½ inches.
*Borne.*—Singly.
*Stems.*—Long; strong.
*Form (when first open).*—High centered. Permanence: Outer petals curl back.
*Petalage.*—Number of petals under normal conditions: From 25 to 30.
*Color.*—Center of flower: When fully open, flower color is very uniform from center to outer petals on both upper and reverse surfaces; Ochraceous Orange, Plate XV, 15′. General tonality from a distance: Ochraceous Orange, Plate XV, 15′.
*Discoloration.*—General tonality at end of first day: Ochraceous Orange, Plate XV, 15′. Third day: Light ochraceous Buff, Plate XV, 15′–d.
*Fragrance.*—Slight. Nature: Fruity.
Petals:
*Texture.*—Thick.
*Surface.*—Inside: Satiny. Reverse: Satiny.
*Shape.*—Round.
*Form.*—Tips slightly recurved and edges slightly quilled.
*Arrangement.*—Loosely imbricated.
*Petaloids in center.*—Few.
*Persistence.*—Drop off cleanly.
*Lasting quality.*—On the plant: Long. As cut flower: Long.

REPRODUCTIVE ORGANS

Anthers: Large; many; regularly arranged around styles.
*Color.*—Yellow.
Filaments (threads): Medium length.
*Color.*—Yellow.
Pollen:
*Color.*—Gold-yellow.
Styles: Loosely separated; uneven length.
Stigmas:
*Color.*—Yellow.
Ovaries: All enclosed in calyx.
Fruit: None observed.

PLANT

Form—Bush.
Growth: Vigorous.
Foliage: Compound of 5 leaflets.
*Size.*—Medium.
*Quantity.*—Normal.
*Color.*—New foliage: Upper side—Deep Yellow Green (2), Plate XXXII, 33″–k, overlaid with Burnt Lake, Plate XII, 71–m. Old foliage: Upper side—Empire Green, Plate XXXII, 33″–m. Under side—Deep Malachite Green, Plate XXXII, 35′.
*Shape.*—Oval pointed.
*Texture.*—Upper side: Leathery. Under side: Smooth.
*Ribs and veins.*—Ordinary.
*Edge.*—Serrated; undulated.
*Serration.*—Single; small,
*Petiole (rachis).*—Color: Green. Under side: Prickly.
*Stipules.*—Medium length; serrated.
*Disease resistance.*—Average resistance to mildew and black-spot, as determined by comparison with other rose varieties grown under the same conditions at Newark, N.Y., U.S.A.

Wood:

*New wood.*—Color: Light green. Bark: Smooth.

*Old wood.*—Color: Green. Bark: Smooth.

Thorns:

*Thorns.*—Quantity: On main stalks from base—Ordinary.—On laterals from stalk—Ordinary. Form: From medium to narrow base; long. Color (when young): Green. Position: Irregular.

*Prickles.*—Quantity: On main stalks—Few. On laterals—Few. Color: Green.

*Short needles.*—Quantity: On main stalks—None. On laterals—None.

I claim:

1. A new and distinct variety of rose plant of the hybrid tea class, substantially as herein shown and described, characterized particularly as to novelty by the unique combination of an upright plant habit, a habit of bearing the flowers on long and strong stems, distinctively well-formed flowers of good substance, said flowers being high-centered in the early stages, while being of imbricated form when fully open, and a distinctive, attractive and uniform orange flower color.

No references cited.

ROBERT E. BAGWILL, Primary Examiner